United States Patent [19]
Killion

[11] Patent Number: 6,139,524
[45] Date of Patent: Oct. 31, 2000

[54] STENT DELIVERY SYSTEM WITH PERFUSION

[75] Inventor: Douglas P. Killion, Maple Grove, Minn.

[73] Assignee: Scimed Life Systems, Inc., Maple Grove, Minn.

[21] Appl. No.: 09/174,283

[22] Filed: Oct. 16, 1998

[51] Int. Cl.⁷ .................................................. A61M 29/00
[52] U.S. Cl. ............................. 604/102; 604/96; 606/194
[58] Field of Search ..................... 604/96, 102; 606/108, 606/191, 194, 1, 198

[56] References Cited

U.S. PATENT DOCUMENTS

| | | | |
|---|---|---|---|
| 4,661,094 | 4/1987 | Simpson | 604/53 |
| 4,732,152 | 3/1988 | Wallsten et al. | 128/343 |
| 5,201,757 | 4/1993 | Heyn et al. | 606/198 |
| 5,360,401 | 11/1994 | Turnland | 604/96 |
| 5,368,566 | 11/1994 | Crocker | 604/101 |
| 5,534,007 | 7/1996 | St. Germain et al. | 606/108 |
| 5,573,509 | 11/1996 | Thornton | 604/102 |
| 5,632,754 | 5/1997 | Farley et al. | 606/159 |
| 5,690,643 | 11/1997 | Wijay | 606/108 |
| 5,700,243 | 12/1997 | Narciso, Jr. | 604/102 |
| 5,702,364 | 12/1997 | Euteneuer et al. | 604/96 |
| 5,891,154 | 4/1999 | Loeffler | 606/108 |

*Primary Examiner*—Wynn Wood Coggins
*Assistant Examiner*—Eric Kline
*Attorney, Agent, or Firm*—Vidas, Arrett & Steinkraus

[57] ABSTRACT

An inventive perfusion catheter is disclosed which allows for the flow of a bodily fluid across the catheter while the catheter delivers a treatment device to a specified bodily location. The inventive perfusion catheter finds particular application in the delivery of a stent. The stent is deployed from a chamber having perfusion openings in the proximal and distal ends. The perfusion openings are constructed and arranged so as to allow the flow of a bodily fluid such as blood through the chamber.

26 Claims, 3 Drawing Sheets

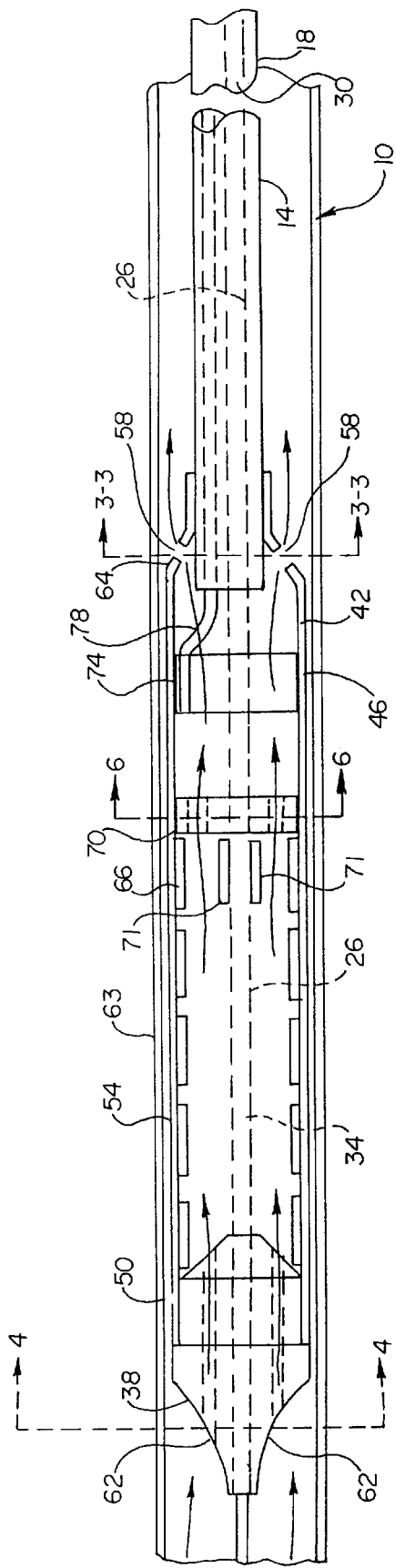
Fig. 2
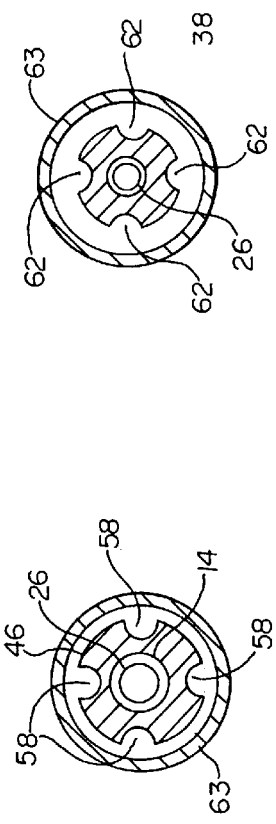
Fig. 3
Fig. 4

STENT DELIVERY SYSTEM WITH PERFUSION

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a balloon expandable stent or a self-expanding stent. For the former type, the stent is often delivered on a balloon and the balloon is used to expand the stent. for the latter type, the self-expanding stents may be made of shape memory materials such as nitinol or constructed of regular metals but of a design which exhibits self expansion characteristics. Self-expanding stents are typically constrained onto the delivery catheter by means of a retractable sheath covering the stent.

It is desirable in performing a PTCA or in implanting a stent to maintain a continuous blood flow across the catheter thereby providing a supply of oxygenated blood downstream from the catheter to prevent or minimize ischemic conditions in tissue distal or proximal to the catheter depending on the location of the catheter in the circulatory system. Specifically, as the catheter is moved into position in the area of a lesion, blood flow across the lesion may be cut off. Using a perfusion catheter, the catheter may remain in place in the region of the lesion for lengthy periods of time without damage to downstream tissue, thereby allowing for careful placement of balloon expandable or self-expanding stents and reducing the need for pre-dilation in order to maintain blood flow across the lesion.

Where the artery to be treated is the carotid artery, the stents used for implantation in the artery are larger than stents typically inserted in coronary arteries. It is desirable in delivering such stents to use a stent delivery system which is as large as is necessary in order to contain the stent within the stent canister region, but has a reduced shaft profile along the remainder of its length. This arrangement is preferred over a constant shaft size delivery system because it allows the physician to use the minimum size guide catheter shaft practical to allow passage of the stent canister while still retaining the ability to perform good contrast dye injections with the stent in position across the target lesion.

Because of the relative sizes of the stent canister and remainder of the catheter shaft, this type of stent delivery system configuration presents new catheter design challenges. The large stent canister, small proximal shaft arrangement, absent perfusion through the stent, would require the use of a pressurized saline flush through the side arm of the guide catheter hemostatic valve to prevent air from entering the guide catheter through the valve during passage of the stent delivery system through the guide catheter. Air is drawn into the guide catheter as a result of a piston effect. Quite simply, the stent canister displaces a large volume of blood as it is advanced through the guide catheter. Because the proximal shaft has a low profile in comparison with the canister, air may be drawn into the guide catheter behind the canister. In such a system, absent perfusion, it is desirable to have a pressurized source of fluid, such as saline solution, attached to the side-arm of the hemostatic valve to ensure that fluid, rather than air, makes up for the volume loss.

In addition to avoiding drawing air into the catheter because of the volume displacement effect, stent delivery catheters also need to be primed to eliminate any air contained within. Such priming, however, can be difficult, in particular in the region of the stent canister, primarily because of flow turbulence caused by the compressed stent, any rear stent bumpers, radio-opaque markers and the configuration of the tip of the catheter.

It is a goal of the present invention to provide a perfusion catheter capable of allowing perfusion across the stent canister portion of the catheter. It is a further goal of the present invention to provide a catheter whose design overcomes the piston effect and eliminates the necessity of having a pressurized supply of fluid to the catheter. It is a further goal of the present invention to provide a self-priming catheter.

These goals are provided for in the inventive perfusion catheter described herein in which perfusion occurs through the stent canister. Perfusion through the stent canister allows blood to readily pass to the proximal side of the stent canister thereby eliminating any canister volume displacement effect which in turn eliminates the need for a pressurized fluid side flush. Perfusion through the stent catheter also allows for self-priming of the stent canister thereby eliminating the need to manually prime the stent canister.

For the purposes of this disclosure, it should be noted that the word 'mount' and variants thereon, as used in reference to mounting a medical device such as a stent on an inner tube, shall refer to the situation where the medical device is in physical contact with the inner tube, whether as a result of crimping or other processes of attaching the medical device to the inner tube. The word shall also encompass the retention of a medical device in place over an inner tube even absent contact between the medical device and the inner tube. For example, a self-expanding stent retained by a sheath over an inner tube shall also considered to be mounted over the inner tube.

SUMMARY OF THE INVENTION

The present invention provides a self-priming perfusion catheter allowing for perfusion of a bodily fluid such as blood across the catheter. In particular, a stent delivery perfusion catheter is disclosed.

In one embodiment, the present invention is directed to a self-priming perfusion catheter comprising an elongated catheter shaft having proximal and distal ends and an inner member such as a tube. At least a portion of the inner member extends beyond the distal end of the catheter shaft. Optionally, at least a portion of the inner member may be carried within the catheter shaft. The catheter further comprises a catheter tip mounted on the distal end of the inner tube and a sheath having proximal and distal ends. The proximal end of the sheath is mounted on the distal end of the catheter shaft. The sheath extends distally to cover the portion of the inner member extending beyond the distal end of the catheter shaft. The distal end of the sheath sealingly abuts the catheter tip to form a chamber defined by the catheter shaft, sheath and catheter tip. The proximal portion of the sheath includes at least one proximal perfusion opening. Finally, the catheter tip includes at least one distal perfusion opening extending from the chamber through the catheter tip, whereby fluid may flow in the at least one distal perfusion opening, through the chamber and out the at least one proximal perfusion opening. Optionally, the catheter may be used for delivering a treatment device, such as a self-expanding stent, to a desired bodily location.

In another embodiment, the invention pertains to a method of delivering a treatment device such as a stent to a desired location in a bodily vessel while maintaining perfusion of the vessel distal to the desired location. The method comprises the steps of providing an inventive perfusion catheter as described above, delivering a treatment device such as a stent using the inventive perfusion catheter to the desired bodily location, retracting the sheath, deploying the treatment device and removing the catheter from the bodily vessel.

An inventive catheter such as the one described above having a chamber with a tapered narrowing transition portion including at least one proximal perfusion opening therein may suitably be used.

The inventive catheter used in conjunction with the inventive method may be a self-priming perfusion catheter which is inserting into a bodily vessel against the flow of blood so that air is forced out of the proximal perfusion openings of the catheter chamber as blood flows in through the distal perfusion opening.

BRIEF DESCRIPTION OF THE FIGURES

FIG. 2 shows a schematic of the canister region of the catheter of FIG. 1, the catheter residing in a guide catheter.

FIG. 3 is a schematic of a transverse cross-sectional view of the catheter shown in FIG. 2 taken along the lines 3—3.

FIG. 4 is a schematic of a transverse cross-sectional view of the catheter shown in FIG. 2 taken along the lines 4—4.

DETAILED DESCRIPTION OF THE INVENTION

Figure 1:
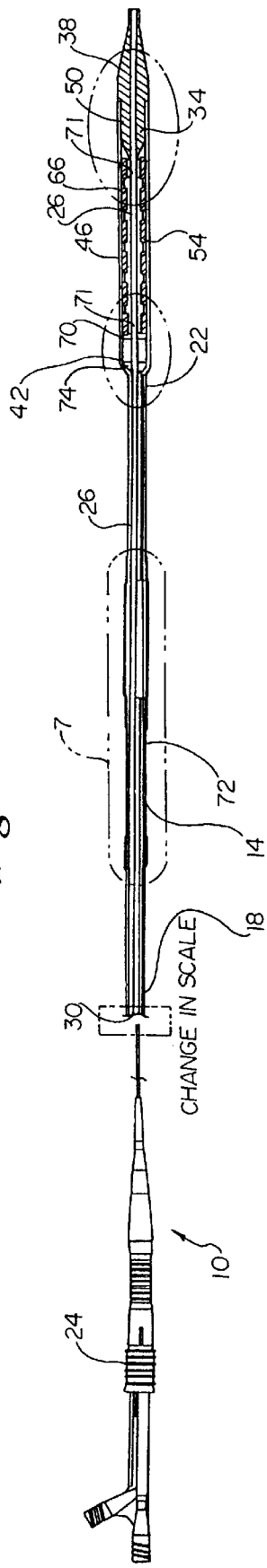
FIG. 1 shows a side-elevational view of an inventive catheter.

While this invention may be embodied in many different forms, there are described in detail herein specific preferred embodiments of the invention. This description is an exemplification of the principles of the invention and is not intended to limit the invention to the particular embodiments illustrated.

FIGS. 1–4 illustrate a perfusion type catheter, shown generally at 10, embodying features of the present invention. The catheter 10 generally includes an elongated catheter shaft 14 having proximal 18 and distal 22 ends. Carried within catheter shaft 14 and extending beyond distal end 22 of catheter shaft 14 is an inner tube 26 of greater length than elongated catheter shaft 14. Inner tube 26 has proximal 30 and distal ends 34. Inner tube 26 is preferably made of flexible, but incompressible construction such as a polymer encapsulated braid or coil. The flexibility of the braid/coil construction allows the catheter to navigate through body lumens and the incompressibility of the braid/coil aids in maintaining the integrity for the catheter and aids in deployment accuracy when the sheath is being retracted during stent release. The braid/coil may be comprised of stainless steel encased in a polymer such as Polyimide with an inner layer of Teflon.

As seen in FIGS. 1 and 2, a catheter tip 38 is affixed to distal end 34 of inner tube 26. An adhesive such as H.B. Fuller 3507, a urethane adhesive, or the like is suitable. Proximal end 42 of sheath 46 is mounted on distal end 22 of catheter shaft 14. The mounting may be accomplished using any suitable adhesive known in the art or through any other suitable means. Sheath 46 may be flexible or rigid, and is generally used to retain a stent 36 and protect the vessel wall. The retractable sheath is preferably formed of a material which provides tensile strength, but is flexible, such as polyethylene. Sheath 46 further has a distal end 50. Sheath 46 extends distally to cover the portion of inner tube 26 extending beyond distal end 22 of catheter shaft 14. Distal end 50 of sheath 46 sealingly abuts catheter tip 38 to form a chamber 54 defined by distal end 22 of catheter shaft 14, sheath 46 and catheter tip 38. The proximal end 42 of sheath 46 includes at least one proximal perfusion opening 58. Catheter tip 38 includes at least one distal perfusion opening 62 extending from chamber 54 through catheter tip 38 allowing fluid to flow in the at least one distal perfusion opening 62, through chamber 54 and out the at least one proximal perfusion opening 58. Also shown in FIG. 2, although not in FIG. 1, is an optional guide catheter 63. Finally, a manifold 24 is secured to the proximal end 18 of catheter shaft 14.

Figure 5:
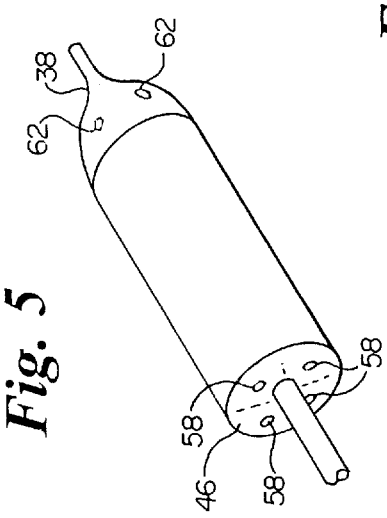
FIG. 5 is a schematic perspective view of the stent canister.

Proximal and distal perfusion openings 58 and 62 are better seen in FIGS. 3 and 4 which present transverse cross-sectional views of the catheter shown in FIG. 2 taken along the lines 3—3 and 4—4 respectively. Specifically, FIG. 3 shows a transverse cross-section through the proximal end of the sheath including four proximal perfusion openings 58 in sheath 46, catheter shaft 14 and inner tube 26 while FIG. 4 shows a transverse cross section through tip 38 including four distal perfusion openings 62 and inner tube 26. Both FIGS. 3 and 4 also show an optional guide catheter 63. FIG. 5 shows a perspective view of the inventive catheter, showing distal perfusion openings 62 in tip 38 and proximal perfusion openings 62 in proximal portion of sheath 46.

Figure 6:
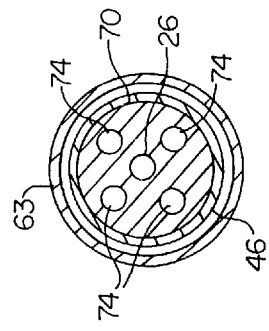
FIG. 6 is a transverse cross-sectional view of the catheter shown in FIG. 2 taken along the lines 6—6.

The inventive perfusion catheter further comprises a treatment device that may be deployed at a desired bodily location. In a preferred embodiment as shown in FIGS. 1 and 2, the treatment device is stent 66 mounted over distal end 34 of inner tube 26 and underneath sheath 46. One or more optional bumpers 70 may abut stent 66. If present, bumpers 70 may have one or more bumper perfusion openings therein as seen in FIG. 6. FIG. 6 shows a transverse cross section of the catheter along line 6—6 including optional guide catheter 63, sheath 46, bumper 70 and inner tube 26 therein. Bumper 70 is shown having four bumper perfusion openings 74 therein. Bumper 70 may be of polyethylene and is affixed to inner tube 26 by adhesive such as H.B. Fuller 3507 so as to prevent movement of stent 66 in a proximal direction when sheath 46 is retracted.

The catheter may further comprise one or more marker bands 71 abutting stent 66. Marker bands 71 are included to aid in positioning and maybe affixed to inner tube 26 by adhesive such as Loctite 4011.

Stent 66 may be self-expanding, mechanically expandable or balloon expandable.

In the case of balloon expandable stents, a balloon (not shown) is mounted over inner tube 26 such that at least a portion of the balloon is underneath stent 66. The balloon is in fluid communication with an inflation lumen for inflating the balloon. A description of an inflation lumen in fluid communication with a balloon may be found in U.S. Pat. No. 5,360,401 to Turnland, incorporated in its entirety herein by reference. Of course, other types of treatment devices may be used as well such as a fiber optic cable in communication with a radiation source or a balloon for angioplasty.

While proximal end 42 of sheath 46 is shown having a tapered narrowing transition portion 64 with proximal perfusion openings 58 therein, the proximal end of the sheath need not be tapered. In another embodiment, the proximal end of the sheath ends in an endcap having proximal perfusion openings therein.

Figure 7:
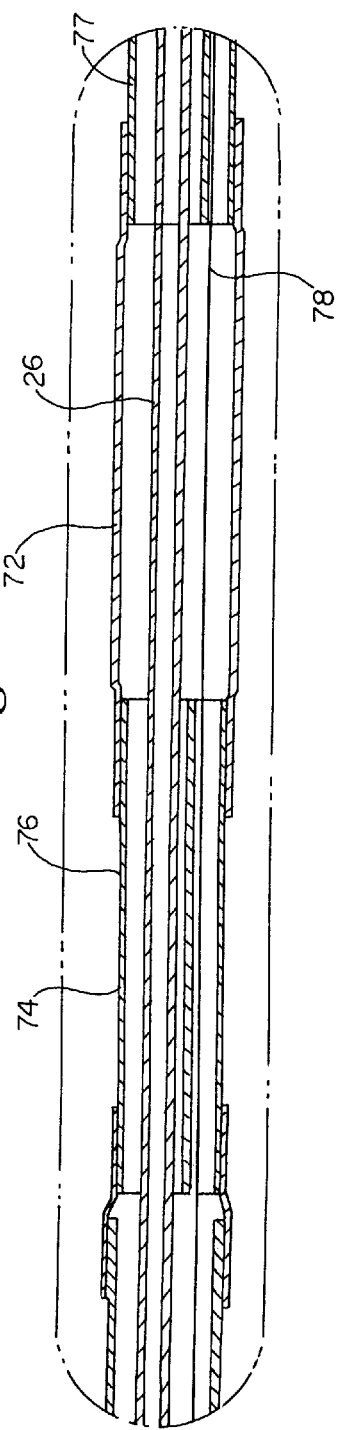
FIG. 7 is an enlarged view of region 7 in FIG. 1.

Sheath 46 in an unretracted position, as shown in FIGS. 1 and 2, covers stent 66 and in the retracted position exposes the stent for deployment. The invention contemplates the use of any suitable means known in the art for retracting the sheath. In the embodiment of the catheter shown in FIG. 1, and further seen in FIG. 7, elongated catheter shaft 14 comprises a number of sections including an accordion-like collapsible section 72, which may be adhesively or otherwise joined to adjacent segments 76 and 77 of the catheter shaft, as described in U.S. Pat. No. 5,534,007 incorporated herein in its entirety by reference. In this embodiment, the sheath is withdrawn by pulling on a pull wire (not shown) attached to the sheath. The pull wire may take the form of the nitinol retraction wire disclosed in commonly owned U.S. patent application Ser. Nos. 08/941,978 and 08/947,619, the entire contents of which are hereby incorporated by reference. The accordion-like section compresses as the sheath, which is attached to the catheter shaft, moves in a proximal direction.

In the embodiment shown in FIG. 2, the perfusion catheter further comprises a pull back mechanism for retracting the sheath. The pull back mechanism, in this case, is a pull collar 74 assembly having a pull wire 78 attached thereto. Pull collar 74 is a ring-shaped member of stainless steel or a radio-opaque substance such as gold affixed to the interior of the sheath by an appropriate adhesive such as Loctite 4011, a cyanoacrylate. The pull wire extends to the proximal end of the catheter and is operatively connected to the sheath. Other suitable pull back mechanisms include screw-like retraction devices as described in U.S. Pat. No. 5,201,757 to Heyn et al. incorporated herein in its entirety by reference. Any other suitable pull back mechanism, as is known in the art, may also be used.

The perfusion catheter may further comprise a balloon mounted thereon, underneath the stent as described in U.S. Pat. No. 5,360,401 to Turnland.

Although not shown in the Figures, in another embodiment of the catheter, the tapered narrowing transition portion of the sheath and more generally, the proximal end of the sheath may be slidably sealed to the distal end of the catheter shaft as described in U.S. patent application Ser. No. 09/071,484 filed May 1, 1998, and U.S.application Ser. No. 08/722,834 filed Sep. 27 1996, both of which are incorporated in their entirety herein by reference Catheter 10 may further include other lumen as well such as a guidewire lumen.

The inventive catheter may be self-priming when inserted in a lumen and exposed to arterial blood pressure and flow.

As shown in FIG. 2, blood entering distal perfusion openings 62 flows through chamber 54 in a proximal direction as indicated by the arrows, through the bumper perfusion openings and forces air out of the chamber through proximal perfusion openings 58.

Also contemplated by the invention is the use of a full-length sheath. Examples of such sheaths are disclosed in U.S. Pat. No. 4,732,152 to Wallsten incorporated herein in its entirety by reference. As applied to the present application, the full length sheath has a region of enlarged diameter corresponding to the region of the stent chamber and a region of reduced diameter proximal to the region on enlarged diameter. The perfusion holes are present on the distal and proximal ends of the region of enlarged diameter. Optionally, a seal may be present either at the proximal end of the region of enlarged diameter or just proximal to the region to prevent blood from flowing along the entire length of the proximal sheath. Such a seal may extend from the sheath to the inner tube.

Figure 8:
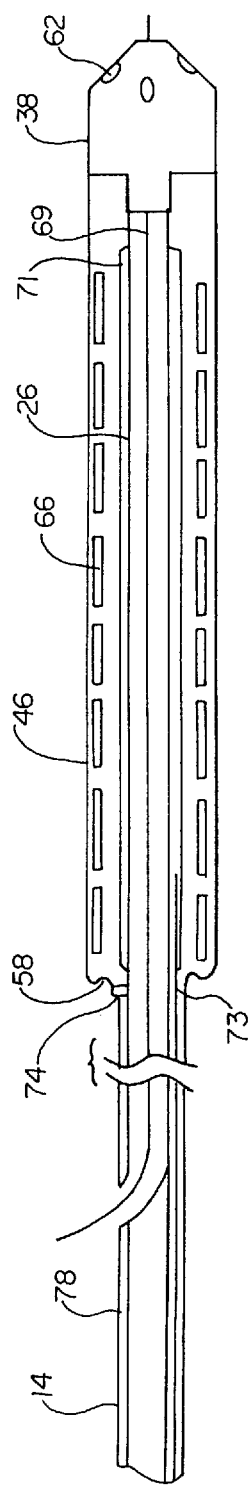
FIG. 8 is a schematic side-elevational view of a rapid exchange version of the inventive catheter.

The invention pertains to a variety of catheters including over the wire catheters, rapid exchange catheters and fixed wire catheters. A schematic illustration of a rapid exchange version of the inventive catheter is shown in FIG. 8. As shown in FIG. 8, a retractable sheath 46 is present at the distal end of catheter shaft 14. Catheter shaft 14 further has a guide wire port 67 proximal to retractable sheath 46 through which guide wire 69 enters the catheter. Guide wire 69 is carried within inner tube 26 which extends from guide wire port 67 to distal tip 38. Distal perfusion holes 62 are present in tip 38. Inner tube 26 optionally has a balloon 71 mounted thereon. Optional balloon 71 is in fluid communication with inflation lumen 73 which extends to the proximal end of the catheter. Stent 66 is mounted over the distal end of inner tube 26 and contained by retractable sheath 46. Retractable sheath 46 has proximal perfusion holes 58 so as to allow for perfusion across chamber 54. Attached to the proximal end of retractable sheath 46 is a pull collar 74 assembly having a pull wire 78 attached thereto. Pull wire 78 extends proximally to a manifold (not shown). Of course, other suitable pull-back mechanisms may be substituted including the accordion sheath disclosed above. Typically, the usable length of the perfusion catheter is approximately 135 cm. For a rapid-exchange catheter the distance from where the guide wire accesses the inner tube to the distal tip will be approximately 5 cm to 35 cm.

A fixed wire version of the inventive catheter may be made by modifying an over-the-wire version of the catheter such that the guide wire is actually fixed to the catheter. The fixed wire catheter disclosed in U.S. Pat. No. 5,702,364 to Euteneuer et al. and incorporated herein its entirety by reference may also be used in conjunction with the present invention to produce a fixed wire perfusion catheter. Other suitable designs for fixed wire catheters known in the art may also be applied to the inventive catheter so as produce an inventive fixed wire perfusion catheter.

The invention also pertains to a method of delivering a stent to a desired location in a bodily vessel while maintaining perfusion of the vessel. The methods involves the steps of providing an inventive perfusion catheter such as that described above, delivering a stent using the inventive perfusion catheter to the desired bodily location, retracting the sheath on the catheter, deploying the stent, and removing the catheter from the bodily vessel.

The invention is further directed to a method of delivering a treatment device to a desired location in a bodily vessel while maintaining perfusion of the vessel distal to the desired location comprising the steps of providing an inventive self-priming perfusion catheter, inserting the catheter into a bodily vessel so that air is forced out of the proximal perfusion openings of the catheter chamber as blood flows in through the distal perfusion openings, delivering the treatment device to the desired bodily location, retracting the sheath, deploying the treatment device, and removing the catheter from the bodily vessel.

In use, catheter 10 may be inserted in a guide catheter and may be advanced over a guidewire into a vessel in a patient in a conventional manner until the treatment device reaches the desired bodily location. Once in position, the guidewire may be removed. Typically, the guide catheter is constructed and arranged so as to have an inner diameter which is only slightly larger than the largest outer diameter of the perfusion catheter, namely, the outer diameter of the sheath covering the treatment device. Desirably, the smallest guide catheter that will accommodate the inventive perfusion catheter is used.

Although the embodiment shown in FIGS. 3, 4 and 6 has four perfusion openings, the precise number of openings, the positioning of the openings and the size of the perfusion openings will depend on the specific dimensions of the catheter and the purpose to which the catheter is put. It is desirable that the proximal and distal perfusion openings as well as any bumper perfusion openings be arranged so as to facilitate substantially longitudinal fluid flow through the catheter. The perfusion openings may be round, elliptical, rectangular or of other suitable shape as is known in the art.

While the invention has been described for use in bodily vessels such as blood vessels, and in particular in the carotid artery, the inventive perfusion catheter may also be used in other bodily lumens through which fluids flow.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A perfusion catheter comprising:
    an elongated catheter shaft having proximal and distal ends;
    an inner member, at least a portion of the inner member extending beyond the distal end of the catheter shaft, the inner member having proximal and distal ends;
    a catheter tip mounted on the distal end of the inner member;
    a sheath having proximal and distal ends, at least a portion of the sheath extending distally to cover at least a portion of the inner member extending beyond the distal end of the catheter shaft, the distal end of the sheath abutting the catheter tip to form a chamber extending between the inner member and the sheath and between the catheter tip and distal end of the catheter shaft, the sheath including at least one proximal perfusion opening in the portion of the sheath that covers at least a portion of the inner tube;
    the catheter tip including at least one distal perfusion opening therethrough opening directly into the chamber,
    whereby fluid may flow through the at least one distal perfusion opening, through the chamber and through the at least one proximal perfusion opening.

2. The perfusion catheter of claim 1 further comprising a stent mounted over the distal end of the inner member and underneath the sheath.

3. The perfusion catheter of claim 2 wherein the sheath is retractable, the sheath in an unretracted position covering the stent and the sheath in the retracted position exposing the stent for deployment.

4. The perfusion catheter of claim 3 further comprising a pull back mechanism for retracting the sheath, the pull back mechanism operatively connected to the sheath.

5. The perfusion catheter of claim 4 wherein the pull back mechanism comprises a pull collar assembly having a pull wire attached thereto, the pull wire extending to the proximal end of the catheter.

6. The perfusion catheter of claim 2 wherein the stent is self-expanding.

7. The perfusion catheter of claim 2 further comprising an inflation lumen at least a portion of which is carried within the catheter shaft and a balloon mounted over the distal end of the inner member at least a portion of the balloon mounted under the stent, the balloon in fluid communication with the inflation lumen, the stent being balloon expandable.

8. The perfusion catheter of claim 2 comprising at least one bumper mounted over the inner tube and abutting the stent, the bumper having at least bumper perfusion opening therein.

9. The perfusion catheter of claim 2 wherein the catheter tip has four distal perfusion openings therein.

10. The perfusion catheter of claim 2 wherein the proximal end of the sheath includes a tapered narrowing transition portion having four proximal perfusion openings therein.

11. A method of delivering a stent to a desired location in a bodily vessel while maintaining perfusion of the vessel distal to the desired location comprising the steps of:
    providing a perfusion catheter as in claim 2;
    delivering the stent using the perfusion catheter to the desired bodily location;
    retracting the sheath;
    deploying the stent;
    removing the catheter from the bodily vessel.

12. The perfusion catheter of claim 1 wherein the inner member is an inner tube having proximal and distal ends, at least a portion of the inner tube carried within the catheter shaft.

13. The perfusion catheter of claim 12 wherein the catheter shaft has a guide wire port therein proximal to the sheath, the proximal end of the inner tube terminating in the guide wire port, the catheter in rapid-exchange form.

14. The perfusion catheter of claim 12 wherein the inner tube extends from the proximal end of the catheter to the distal end, the catheter in over-the-wire form.

15. The perfusion catheter of claim 1 which is self priming when inserted in a bodily vessel and exposed to arterial blood pressure, whereby blood entering the at least one distal perfusion opening forces air out of the chamber through the at least one proximal perfusion opening.

16. The perfusion catheter of claim 1 wherein the catheter is a fixed wire catheter and the inner member is an inner tube, the catheter further comprising a guide wire, at least a portion of which is carried within the inner tube.

17. The perfusion catheter of claim 1 in combination with a guidewire.

18. The perfusion catheter of claim 1 wherein the sheath extends distally from the distal end of the catheter shaft and the proximal end of the sheath includes a tapered narrowing transition portion, the at least one proximal perfusion opening extending through the tapered portion.

19. The perfusion catheter of claim 1 in combination with a guide catheter, the catheter shaft and sheath each having an outer diameter less than the inner diameter of the guide catheter.

20. The perfusion catheter of claim 1 wherein the sheath is a full length sheath extending proximally over the proximal end of the catheter shaft.

21. A method of delivering a treatment device to a desired location in a bodily vessel while maintaining perfusion of the vessel distal to the desired location comprising the steps of:

provided a self-priming perfusion catheter having
an elongated catheter shaft having proximal and distal ends;
an inner member, at least a portion of the inner member extending beyond the distal end of the catheter shaft, the inner member having proximal and distal ends;
a catheter tip mounted on the distal end of the inner member;
a retractable sheath having proximal and distal ends, the proximal end of the sheath mounted on the distal end of the catheter shaft, the sheath extending distally to cover the inner member extending beyond the distal end of the catheter shaft and the distal end of the sheath abuts the catheter tip to form a chamber extending between the inner member and the sheath and between the catheter tip and distal end of the catheter shaft, the chamber including a tapered narrowing transition portion including at least one proximal perfusion opening;
the catheter tip including at least one distal perfusion opening therethrough opening directly into the chamber; and
a treatment device located at the distal end of the catheter shaft within the chamber;

inserting the catheter into a bodily vessel against the flow of blood so that air is forced out of the proximal perfusion openings of the catheter chamber as blood flows in through the distal perfusion openings;
delivering the treatment device to the desired bodily location;
retracting the sheath;
deploying the treatment device;
removing the catheter from the bodily vessel.

22. The method of claim 21 wherein the treatment device is a stent mounted over the distal end of the inner tube.

23. The method of claim 22 where the stent is self expanding.

24. The method of claim 22, the catheter further comprising an inflation lumen at least a portion of which is carried within the catheter shaft, and an inflatable balloon mounted over the distal end of the inner tube, at least a portion of the balloon underneath the stent, the balloon in fluid communication with the inflation lumen, the stent being balloon expandable.

25. The method of claim 21 wherein the treatment device comprises a fiber optic cable in communication with a radiation source.

26. A perfusion catheter comprising:
an elongated catheter shaft having proximal and distal ends;
an inner member, at least a portion of the inner member extending beyond the distal end of the catheter shaft, the inner member having proximal and distal ends;
a catheter tip mounted on the distal end of the inner member;
a sheath having proximal and distal ends, the proximal end of the sheath mounted on the distal end of the catheter shaft, the sheath extending distally to cover the portion of the inner member extending beyond the distal end of the catheter shaft and the distal end of the sheath abutting the catheter tip to form a chamber extending between the inner member and the sheath and between the catheter tip and distal end of the catheter shaft, the proximal end of the sheath including at least one proximal perfusion opening;
the catheter tip including at least one distal perfusion opening therethrough opening directly into the chamber,
whereby fluid may flow through the at least one distal perfusion opening, through the chamber and through the at least one proximal perfusion opening.

* * * * *